(12) United States Patent
Mascarenhas

(10) Patent No.: US 8,761,867 B2
(45) Date of Patent: Jun. 24, 2014

(54) METHOD AND SYSTEM FOR REDUCING POWER LINE INTERFERENCES IN AN ECG SIGNAL

(75) Inventor: Dinesh Leo Mascarenhas, Karnataka (IN)

(73) Assignee: General Electric Company, Schenectady, NY (US)

( * ) Notice: Subject to any disclaimer, the term of this patent is extended or adjusted under 35 U.S.C. 154(b) by 310 days.

(21) Appl. No.: 12/851,576

(22) Filed: Aug. 6, 2010

(65) Prior Publication Data

US 2011/0066052 A1     Mar. 17, 2011

(30) Foreign Application Priority Data

Sep. 16, 2009   (IN) ............................ 2253/CHE/2009

(51) Int. Cl.
*A61B 5/0402*     (2006.01)

(52) U.S. Cl.
USPC ......................................................... 600/509

(58) Field of Classification Search
USPC .................. 600/508–509, 512, 523–524
See application file for complete search history.

(56) References Cited

U.S. PATENT DOCUMENTS

| | | | |
|---|---|---|---|
| 6,219,392 B1 | 4/2001 | Abe | |
| 6,282,440 B1 * | 8/2001 | Brodnick et al. | 600/512 |
| 6,351,664 B1 * | 2/2002 | Brodnick | 600/509 |
| 2001/0007433 A1 * | 7/2001 | Abe | 327/552 |
| 2008/0275353 A1 | 11/2008 | Bartal et al. | |

FOREIGN PATENT DOCUMENTS

| | | |
|---|---|---|
| CN | 1658501 A | 8/2005 |
| CN | 101297754 A | 11/2008 |
| CN | 101385645 A | 3/2009 |

OTHER PUBLICATIONS

Tompkins, Willis J. "(A) Adaptive Canceling Using a Sine Wave Model approach to removing sine wave interference," Biomedical Signal Processing. Mar. 2, 1993, Prentice Hall (textbook).
Unofficial translation of CN Office Action for CN Application No. 201010293511.9, dated Dec. 11, 2013.
Unofficial translation of CN Search Report for CN Application No. 201010293511.9, dated Dec. 4, 2013.

* cited by examiner

*Primary Examiner* — Rex R Holmes
(74) *Attorney, Agent, or Firm* — Global Patent Operation; Marc A. Vivenzio

(57) ABSTRACT

A method and system for correcting power line interferences in an ElectroCardioGram (ECG) signal is disclosed. The method comprises: providing an input signal having ECG signal along with interference signals to a digital filter capable of filtering at a preset frequency and identifying current power line frequency, if any, from the filtered input signal. The method further includes providing a look up table with index number for a set of frequency levels and corresponding filter coefficients, the set of frequency includes incremental steps in the range of possible variations on the power line frequency. The filter coefficient corresponding to current power line frequency is identified from the look up table. The digital filter is configured using the identified filter coefficient and the input signal is filtered using the re-configured digital filter.

12 Claims, 4 Drawing Sheets

METHOD AND SYSTEM FOR REDUCING POWER LINE INTERFERENCES IN AN ECG SIGNAL

FIELD OF INVENTION

This invention relates generally to noise reduction techniques in an ECG device and more particularly to, a method and system for reducing power line interferences in an ECG signal.

BACKGROUND OF INVENTION

The interference of noise signal on an ECG signal is significant as it may affect the quality of the signal and may result in wrong clinical interpretation. One of the sources of the noise in the ECG signal is the power fluctuations and the interference from the power transmission line. Line frequency variation is common in many developing countries where ECG products are used for diagnostic purposes. Generally, the powerline frequency is expected to be 50 Hz or 60 Hz and this value is country specific. In some places the frequency varies from the set value.

Some of the solutions suggest eliminating the noise in ECG signals, but at least a part of the ECG signal is also removed, while removing the noise. Thus clinically relevant information is lost from the ECG signal. Existing line frequency filters do eliminate the line frequency well as long as it does not vary. In an example, when the variation exceeds more than ±0.5 Hz, the efficacy of the filter is markedly reduced.

Some of the techniques for eliminating noise includes band limiting the signal to below the powerline frequency by using low pass filters, but this will result in loss of information since attenuation is done for all frequencies above 50/60 Hz.

A notch filter at 50 Hz/60 Hz is used for eliminating the noise. This will result in removal of the powerline interference but will also remove the 50 Hz/60 Hz component present in the ECG signal. Though this may be better option, using notch filters can cause ringing in the ECG waveform, which can result in wrong interpretation and analysis of the signal.

Some examples of adaptive filters studied, would filter the powerline frequency without affecting the ECG signal, but were not effective in the face of variations in frequency.

Thus it will be beneficial to have an improved method for eliminating power line interferences in an ECG signal.

SUMMARY OF INVENTION

The above-mentioned shortcomings, disadvantages and problems are addressed herein which will be understood by reading and understanding the following specification.

One embodiment of the present invention provides a method of correcting power line interferences in an Electro-CardioGram (ECG) signal. The method comprises: providing an input signal having ECG signal along with interference signals to a digital filter capable of filtering at a preset frequency; identifying current power line frequency from the filtered input signal; providing look up tables with index number for a set of frequency levels and corresponding filter coefficients, the index number includes incremental steps in the range of possible variations on the power line frequency; identifying filter coefficient corresponding to current power line frequency from the look up table; configuring the digital filter using the identified filter coefficient; and filtering the input signal with the digital filter, the digital filter being re-configured using the identified filter coefficient.

In another embodiment, a system for correcting power line interferences in an ECG signal is disclosed. The system comprises: a configurable adaptive digital filter configured to filter an input signal at a preset frequency, the input signal includes an ECG signal with power line interference signal; a line frequency identifier configured to identify current power line frequency from the input signal, filtered by the digital filter; a memory having frequency table of index number for set of frequency levels covering the range of possible power line frequency variations and a coefficient table having filter coefficients corresponding to each level in the frequency table; a control unit configured to identify a filter coefficient corresponding to the current line frequency identified by the line frequency identifier; wherein the control unit is configured to configure the adaptive filter dynamically with the identified filter coefficient for filtering the input signal.

In yet another embodiment, an ECG device comprises: a monitor; a lead wire assembly for capturing an ECG signal, wherein the ECG signal includes power line interference signal; a processor for processing the ECG signal; and a memory; wherein the processor is configured to filter the ECG signal, the filtering being done based on a filter coefficient identified in real time corresponding to current power line frequency.

Various other features, objects, and advantages of the invention will be made apparent to those skilled in the art from the accompanying drawings and detailed description thereof.

DETAILED DESCRIPTION OF INVENTION

Figure 1:
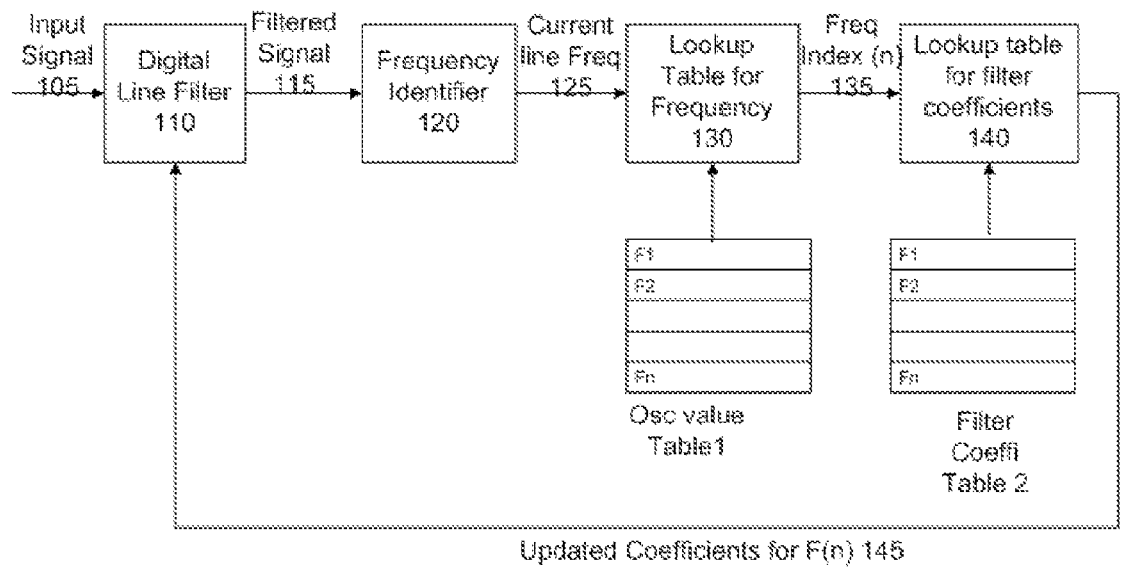
FIG. 1 is a schematic diagram for reducing power line interference as described in an embodiment of the invention.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

An embodiment of the invention provides a method and system for reducing the power line interference in an input signal, in an example an ECG signal. A dynamically configurable adaptive digital filter is configured to filter the input signal, the filter coefficients of the digital filter being configured in real time, based on the filter coefficients selected from a look up table with reference to the current power line frequency. The interference signal is a sinusoidal signal like power line or power supply signal with unknown frequency.

FIG. 1 is a schematic diagram for reducing power line interferences in an input signal as described in an embodiment of the invention. The scheme includes providing an adaptive digital line filter 110 configured to filter an input signal at a set frequency. The input signal includes a desired signal such as ECG signal along with noise signals such as power line interference. The digital line filter 110 could be an adaptable filter programmable by altering the filtering coefficients of the filter 110. During initial stage of signal processing, the digital filter is configured to filter at a pre set frequency, for example, at expected power line frequency such as 50 Hz or 60 Hz. The digital filter filters the input signal and if the filter coefficient matches with the current power line frequency, the filtered input signal will be free of power line interference. However if there is any variation in the line frequency, the filtered signal will include the interference signal as well.

In an embodiment, the current line frequency or fluctuation in the power line frequency is identified and the digital filter is configured in real-time to eliminate the interference signal identified. This is achieved using a frequency identifier 120 provided along with look up tables 130, 140. A frequency-computing algorithm or circuitry could be used to identify the frequency of an input signal such as an ECG signal. The output of the digital filter 110 is provided to the frequency identifier 120. In the event of frequency fluctuation, the input signal i.e filtered signal 115 to the frequency identifier 120 will be same as the input signal 105 to the digital filter 110. The filtered signal 115 includes ECG signal and the interference signal and is provided to the frequency identifier 120 and the frequency identifier 120 identifies the frequency of the filtered signal 115 or the sinusoidal signal i.e the frequency of the interference signal or the power line frequency.

The look up tables 130, 140 includes a frequency table 130 and a filter coefficient table 140. The frequency table 130 includes index number indicating incremental steps in the range of possible variations on the power line frequency. By taken into consideration, the typical range in which the line frequency varies from its intended preset value (±F) and the affectivity of the filter from its set value (±Df, N levels are defined, where, $N=(2 \times F)/Df+1$.

Once the frequency of the interference signal or the current power line frequency 125 is identified, the identified frequency 125 is provided to the frequency table. The frequency identified by the frequency identifier is approximated with different levels of frequency provided in the frequency table 130. The identified line frequency will be approximated to the closest frequency index, represented as Freq Index (n) 135 in the frequency table. The method uses an optimized method to find the most appropriate fit for the identified frequency with one of the N levels. Corresponding to each index number or Freq Index (n) in the frequency table 130, filter coefficients are calculated and provided in the coefficient table 140. The filter coefficient value is calculated based on the digital filter design, input signal etc. Thus from the coefficient table, filter coefficients corresponding to the selected frequency Index 135 is identified, represented as updated filter coefficients 145.

Upon identifying a sinusoidal interference signal, the amplitude of the interference signal is checked. If the amplitude of the interference signal exceeds a threshold value, the frequency of the interference signal is compared with the frequency table defined, to get the frequency index with nearest match to the identified frequency. If no match is found then no action is taken, else the index is used to find the new filter coefficient corresponding to the actual power line frequency. The updated filter coefficients 145 are provided to the digital filter 110. Based on the noise reduction requirement, the threshold value of the amplitude could be defined. In an example, the amplitude threshold is defined as 60 µV.

In an embodiment, the digital filter is capable of removing the interference signal completely. In an exemplary embodiment, the interference signal having a peak to peak amplitude if 10 µV is removed using the digital filter.

The digital filter 110 is configured using the updated filter coefficients 145. Thus the digital filter 110 is configured to filter at an updated frequency. This updated frequency is the current line frequency and filtering at the current line frequency will eliminate the power line interference, which is having the current power line frequency. Thus the digital filter 110 will dynamically shift to any of the N frequency levels ensuring elimination of the powerline interference in the band ±F.

Figure 2:
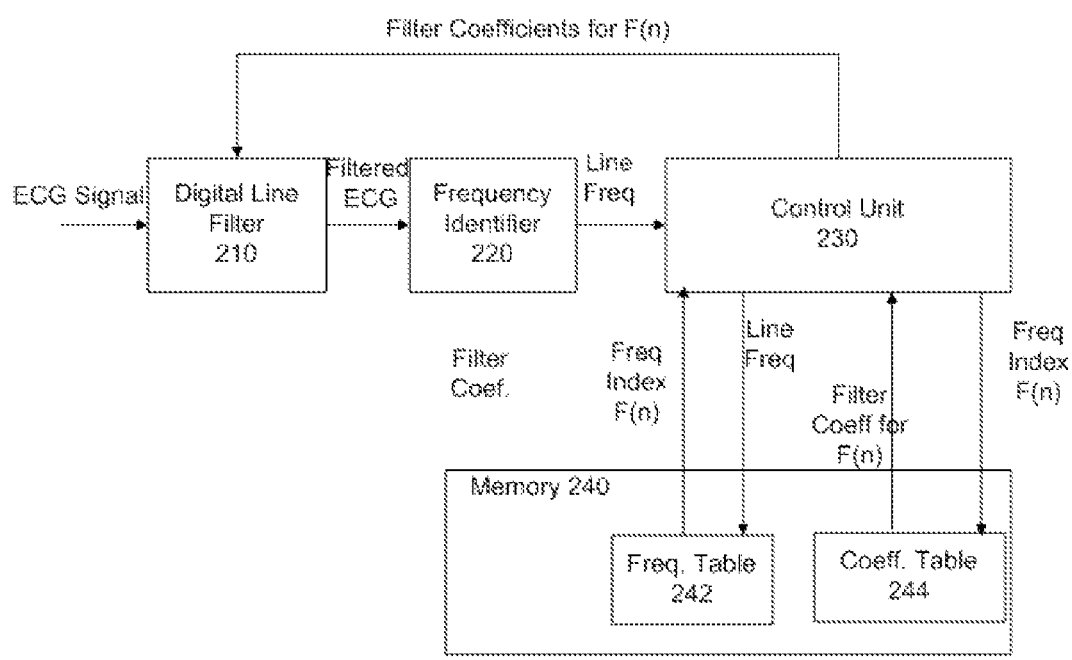
FIG. 2 is a block diagram of a power line interference reduction system as described in an embodiment of the invention.

FIG. 2 is a block diagram of power line interference correction system 200 as described in an embodiment of the invention. ECG signal from an ECG device is provided to the interference correction system. The ECG signal includes various noise interference signals including the interference signal generated due to fluctuation in the power line frequency. The power line interference signal will be a sinusoidal signal having a frequency close to the power line frequency. Since the power fluctuations are very frequent, the interference correction needs to be done in real time. The system 200 comprises an adaptive digital line filter 210. The filter 210 is configurable dynamically by updating filter coefficients in real time. The filter 210 is configured to filter the interference signal generated due to power line frequency from the ECG signal. Generally, the filter 210 is configured at a desired frequency, presumably its the expected line frequency i.e 50 or 60 Hz. If there is no change in the line frequency, the filter will filter the ECG signal and the interference signal will be removed. However due to power line interference, the line frequency changes and hence the digital filter 210 which is configured at a preset frequency will not be able to filter the ECG signal efficiently.

From the filtered ECG signal, wherein the interference signal is present, a frequency identifier 220 identifies the current line frequency. In an embodiment, the current line frequency can be identified by using an oscillator. In an embodiment, the frequency of the interference signal could be identified by the oscillator using the following method. The input EGG signal with interference noise from the power lines is sampled. The interference signals have different amplitude and frequency, but could be overlapped with the ECG signal. The frequency, amplitude and phase of the interference signal are approximated using the oscillator and additional feedback circuitry and thereafter the interference signal could be separated from the ECG signal.

The current power line frequency identified by the frequency identifier 220 is provided to a control unit 230. The control unit 230 could be a part of the power line interference correction system 200 or could be the part of the ECG device. The control unit 230 accesses a memory 240 configured to store lookup tables. The look up table includes frequency look up table 242 and a coefficient lookup table 244. The frequency look up table 242 includes a set of frequency levels including incremental steps in the range of possible variations on the power line frequency. The coefficient look up table 244 includes filter coefficients corresponding to each frequency level in the frequency table. The frequency levels and corresponding filter coefficients could be defined based on the expected frequency fluctuation and the value of the incremental step would depend the characteristic of the digital filter used for filtering. These lookup tables are programmable and based on the expected frequency fluctuations, the levels or corresponding coefficients can be programmed. The interference correction system 200 can have a separate memory or the memory could be part of the ECG device.

The control unit 230 first checks the amplitude of the interference signal and if the amplitude is above a threshold value then control unit 230 accesses the frequency levels corresponding to the identified or the current power line frequency from the frequency table 242 in the memory 240. The control unit 230 applies the approximation technique and identifies the frequency level, Freq Index F(n) corresponding to the identified power line frequency. Once the frequency level is identified, corresponding filter coefficient Filter Coeff F(n) is identified from the coefficient table 244 in the memory 240. The control unit 230 communicates the selected coefficients to the digital filter 210. The control unit 230 configures the filter 210 dynamically based on the selected coefficients. Since the selected filter coefficient corresponds to the current power line frequency, the filter 210 is configured to filter the signal at the current line frequency. Thus an interference free ECG signal is generated. This process is done iteratively and is performed in real time.

The control unit 230 may include dedicated hardware, software and/or firmware for performing information processing, or a combination of dedicated hardware and software, or software in combination with a general purpose processor, or a digital signal processor. Once the requirements for such software and/or hardware and/or dedicated hardware are gained from an understanding of the descriptions of embodiments of the invention contained herein, the choice of any particular implementation may be left to a hardware engineer and/or software engineer. However, any dedicated and/or special purpose hardware or special purpose processor is considered subsumed in the block labeled control unit 230. The memory 240 may include, for example, random access memory (RAM), flash memory, or read-only memory. For purposes of simplicity, devices that can read and/or write media on which computer programs are recorded are also included within the scope of the term "memory."

Figure 3:
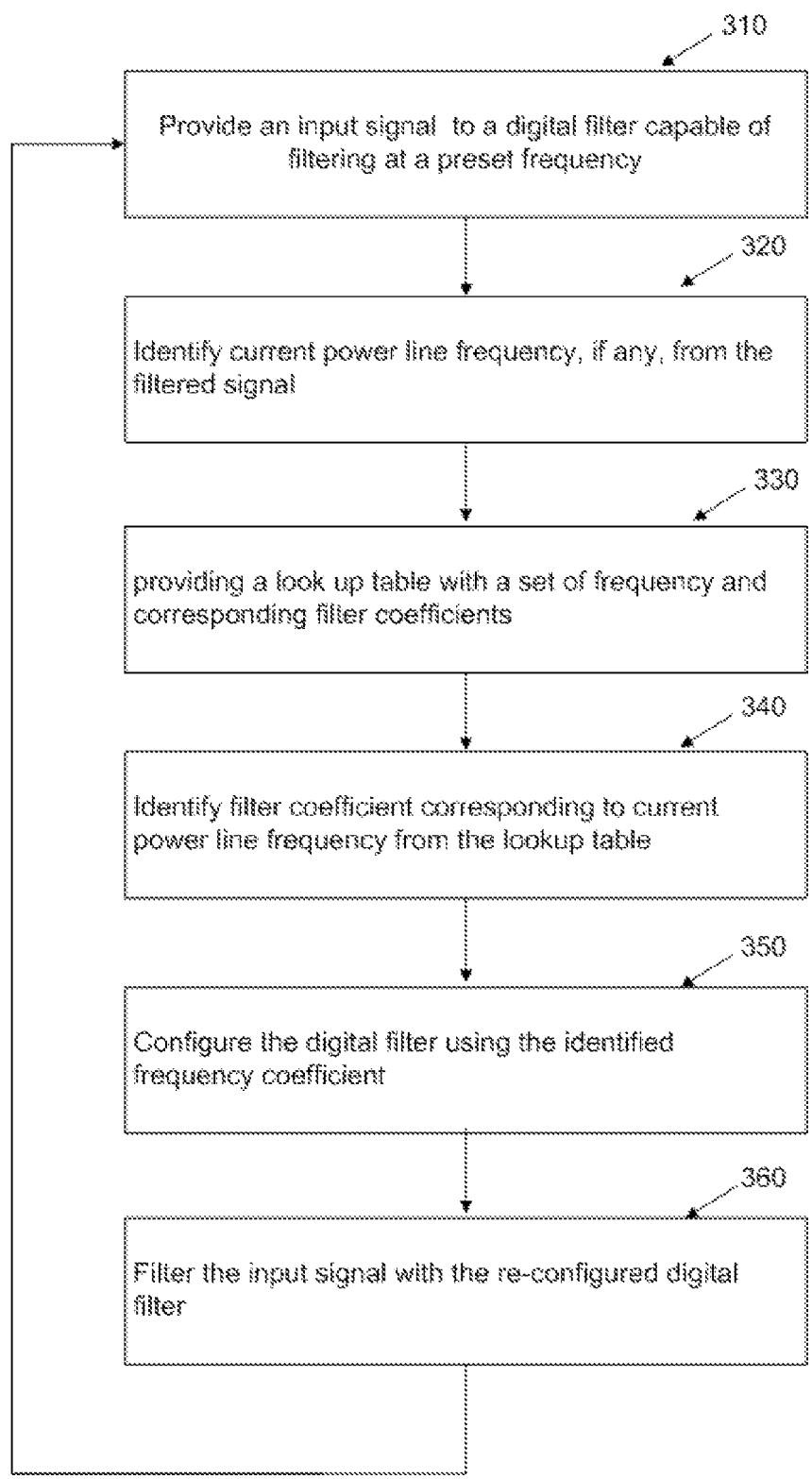
FIG. 3 is a flowchart illustrating a method of correcting power line interferences in an ECG signal, as described in an embodiment of the invention.

FIG. 3 is a flowchart illustrating a method of correcting power line interferences in an ECG signal, as described in an embodiment of the invention. At step 310, an input signal having ECG signal along with an interference signal generated from the power line signal, is provided to a digital filter capable of filtering the input signal at a preset frequency. Generally the filter is configured to filter the input signal at normal power line frequency, generally 50 Hz or 60 Hz. At step 320, the current power line frequency is identified from the input signal. The input signal includes ECG signal along with the power line interferences at current line frequency. From the input signal, current power line frequency is identified. At step 330, a look up table is provided with an index number for a set of frequency and corresponding filter coefficients. The index number includes incremental steps in the range of possible variations on the power line frequency. The identified power line frequency will be matched with the closest frequency level in the frequency table. Corresponding to different levels in the frequency table filter coefficients are provided in the filter coefficient table. At step 340, a filter coefficient corresponding to the line frequency or the identified frequency level from the frequency table is identified. The filtering coefficient is provided to the digital filter. At step 350, the digital filter is configured using the identified filter coefficient and at step 360, the input signal is filtered using the dynamically configured digital filter.

Figure 4:
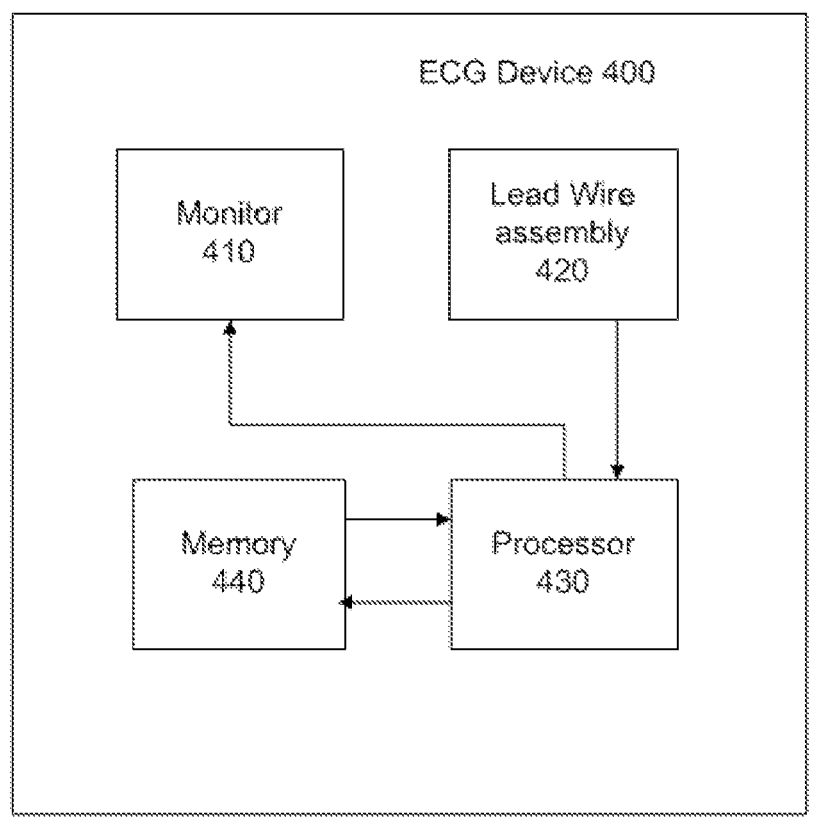
FIG. 4 is a block diagram of an ECG device with a noise reduction system as described in an embodiment of the invention.

FIG. 4 is a block diagram of an ECG device with a noise reduction system as described in an embodiment of the invention. The device 400 comprises a monitor 410, a lead wire assembly 420 and a processor 430. The lead wire assembly 420 is configured to gather data from the patients and the processor 430 processes this data and is displayed or printed using the monitor 410. In an embodiment, the processor 430 has an adaptive digital filter configured to filter the power line interference signal. The filter is configured in real time using filter coefficients derived based on the current power line frequency. The current power line frequency is identified and the filter is configured using the same to eliminate the interference signal at the current power line frequency. The processor 430 may be further configured to identify the current power line frequency and based on that generate the filter coefficient corresponding to the same. The processor 430 interacts with a memory 440 in this regard. The memory 440 is configured to store different levels of frequency along with the corresponding filter coefficients. The processor 430 accesses the memory 440 and based on the current line frequency, matching frequency level and corresponding filter coefficient is selected and the digital filter is configured using the same.

The device is a closed loop system where the output of filter that remove interference for a set frequency is given as input to a frequency identifier which operates through a process of updating the current power line frequency through an iterative process. The current power line frequency value is then compared with a look up table of N frequency levels, for a match with the frequency in a region of interest. If a match is found then another table is referenced and new coefficient for the filter is obtained corresponding to the matched value of frequency.

Thus a method and system for reducing noise in an ECG signal is disclosed herein. The interference caused by the line frequency is identified. The method includes filtering the power line interference from the ECG signal at a set frequency. Amplitude and frequency of the power line frequency is measured. If power line interference is present, filter coefficients for new frequency value/current power line frequency is identified and using the coefficients, the filter performs the filtering option. This is done at real time.

This invention is to eliminate the power line interference from an ECG signal, without removing the same frequency component, which may be part of the ECG signal. The power line frequency is expected to be 50 Hz or 60 Hz and this value is country specific. The power line interference system implemented can track the variation in the line frequency and eliminate the same. The filter is implemented to act on data at real time without the need to buffer the data. By introducing the adaptive filter feature we can effectively remove line noise from 47 Hz to 53 Hz, when line filter is set to 50 Hz and from 57 Hz to 63 Hz when set to 60 Hz. The variation if present, the interference will typically fall in this band. The range if needed can be increased easily.

Since power line interference is one of the most common sources of noise in an ECG and variation in the powerline frequency is common in many developing nations, the method described ensures a better quality ECG and better interpretation of the waveform manually or by interpretation algorithms.

For effectively removing power line interference by maintaining full fidelity of the ECG data, the system requires very effective implementation of adaptive filters, which fit well into the signal chain to give real time performance.

Embodiments of the present invention can comprise software or firmware instructing a computer to perform certain actions. Some embodiments of the present invention comprise stand-alone workstation computers that include memory, a display, and a processor along with the cellular service provider. Whether a stand-alone workstation or a healthcare service management system is used, software and/or firmware (hereinafter referred to generically as "software") can be used to instruct the computer to perform the inventive combination of actions described herein. Portions of the software may have specific functions, and these portions are herein referred to as "modules". However, in some embodiments, these modules may comprise one or more electronic hardware components or special-purpose hardware components that may be configured to perform the same purpose as the software module or to aid in the performance of the software module. Thus, a "module" may also refer to hardware or a combination of hardware and software performing a function.

As used herein, an element or step recited in the singular and proceeded with the word "a" or "an" should be understood as not excluding plural elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Moreover, the terms "computer" and "processor" are used interchangeably herein to refer to either specialized hardware to perform digital signal processing, control, data manipulation, and/or calculations, or a general purpose computer that can be programmed to perform the same functions and/or adapted to interface with external digital signals.

Exemplary embodiments are described above in detail. The assemblies and methods are not limited to the specific embodiments described herein, but rather, components of each assembly and/or method may be utilized independently and separately from other components described herein. Further the steps involved in the workflow need not follow the sequence in which there are illustrated in figures and all the steps in the work flow need not be performed necessarily to complete the method.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

I claim:

1. A method of correcting power line interferences in an ElectroCardioGram (ECG) signal comprising:
    providing an input signal comprising an ECG signal and an interference signal to a digital filter configured to filter the input signal at a an initial preset frequency, the digital filter comprising an adaptive digital line filter with configurable filter coefficients;
    identifying a current power line frequency, if any, from the filtered input signal;
    providing a frequency look up table with a frequency index number for each frequency in a set of different frequency levels and a filter coefficient table with filter coefficients corresponding to each frequency index number, the set of frequency levels including incremental steps in the range of possible variations on the power line frequency;
    determining if an amplitude of the interference signal is above a threshold value; and if so,
    approximating the identified line frequency to a frequency index number in the frequency look up table corresponding to a closest frequency level to the identified current power line frequency;
    identifying a filter coefficient from the filter coefficient table corresponding to the identified frequency index number;
    re-configuring the digital filter using the identified filter coefficient; and
    filtering the input signal with the re-configured digital filter to correct the power line interference,
    wherein the reconfigured digital filter filters the input signal at a frequency corresponding to the identified current power line frequency in real time without buffering data.

2. The method as claimed in claim 1, wherein the interference signal is a sinusoidal signal.

3. The method as claimed in claim 1, wherein filtering the input signal with the re-configured digital filter comprises: obtaining an interference free ECG signal upon matching the filter coefficient of the digital filter with the current power line frequency.

4. The method as claimed in claim 1, wherein the digital filter is re-configured dynamically in real time, based on the current power line frequency obtained from the filtered input signal.

5. The method as claimed in claim 1, wherein the method further comprises: eliminating the interference signal if an amplitude of the interference signal is above a threshold value.

6. The method as claimed in claim 1, wherein providing the frequency look up table comprises: providing a frequency range of N discrete levels and filter coefficients corresponding to each frequency level, wherein $N=(2\times F)/Df+1$, $+/-F$ is the range from the preset frequency, Df is the step size for quantization of the frequency range, depending on the filter characteristics.

7. A system for correcting power line interferences in an ECG signal, the system comprising:
    a configurable adaptive digital filter configured to filter an input signal at a preset frequency, the input signal comprising an ECG signal and a power line interference signal;
    a line frequency identifier configured to identify a frequency of the power line interference signal, if any, from the filtered input signal;
    a memory comprising:
    a frequency table including a set of different frequency levels, the frequency table including an index number corresponding to each frequency level in the set of frequency levels, the set of different frequency levels covering a range of possible power line frequency variations; and
    a coefficient table with filter coefficients corresponding to each frequency level in the set of frequency levels; and a control unit configured to:
  compare an amplitude of the power line interference signal against a threshold value, and if the amplitude exceeds the threshold value:
    identify a filter coefficient corresponding to a frequency level from the frequency table that corresponds to the frequency of the power line interference signal identified by the line frequency identifier; and
  configure the adaptive digital filter dynamically with the identified coefficient for filtering power line interference signal from the input signal
  wherein the frequency lookup table comprises: a frequency range of N levels and frequency coefficients corresponding to each level, wherein N=(2×F)/Df+1, +/−F is the range from the preset frequency, Df is the step size for quantization of the frequency range, depending on characteristics of the configurable adaptive digital filter, and
  wherein the configurable digital filter dynamically shifts to any of the N levels to eliminate power line interference in the band +/−F.

8. The system as claimed in claim 7, wherein the configurable adaptive digital filter is re-configured to a frequency value updated with a filter coefficient corresponding to the current power line frequency level selected from the coefficient table.

9. The method of claim 1, wherein the identified frequency of the power line interference signal is provided to the frequency look up table and approximated to a closest frequency level in the frequency look up table a frequency index number corresponding to the closest frequency level being used to identify the filter coefficient.

10. The method of claim 1, wherein the re-configured digital filter is configured to filter at an updated frequency that corresponds to the frequency of the power line interference signal, wherein filtering at the frequency of the power line interference signal substantially eliminates the power line interference signal.

11. The method of claim 1, wherein the interference signal is a sinusoidal interference signal.

12. A method of correcting power line interferences in an ElectroCardioGram (ECG) signal comprising:
  providing an input signal comprising an ECG signal and an interference signal to a digital filter configured to filter the input signal at a an initial preset frequency, the digital filter comprising an adaptive digital line filter with configurable filter coefficients;
  identifying a current power line frequency, if any, from the filtered input signal;
  providing a frequency look up table with a frequency index number for each frequency in a set of different frequency levels and a filter coefficient table with filter coefficients corresponding to each frequency index number, the set of frequency levels including incremental steps in the range of possible variations on the power line frequency;
  determining if an amplitude of the interference signal is above a threshold value; and if so,
  approximating the identified line frequency to a frequency index number in the frequency look up table corresponding to a closest frequency level to the identified current power line frequency;
  identifying a filter coefficient from the filter coefficient table corresponding to the identified frequency index number;
  re-configuring the digital filter using the identified filter coefficient; and
  filtering the input signal with the re-configured digital filter to correct the power line interference,
  wherein the threshold value of the amplitude is 60 μV.

* * * * *

UNITED STATES PATENT AND TRADEMARK OFFICE
CERTIFICATE OF CORRECTION

PATENT NO. : 8,761,867 B2  
APPLICATION NO. : 12/851576  
DATED : June 24, 2014  
INVENTOR(S) : Mascarenhas It is certified that error appears in the above-identified patent and that said Letters Patent is hereby corrected as shown below:

In the Claims:

In Column 8, Line 1, in Claim 1, delete "at a an" and insert -- at an --, therefor.

In Column 9, Line 12, in Claim 7, delete "signal" and insert -- signal, --, therefor.

In Column 10, Line 10, in Claim 12, delete "at a an" and insert -- at an --, therefor.

Signed and Sealed this
Sixteenth Day of September, 2014

Michelle K. Lee
*Deputy Director of the United States Patent and Trademark Office*